United States Patent [19]
Oh et al.

[11] Patent Number: 5,849,599
[45] Date of Patent: *Dec. 15, 1998

[54] METHOD FOR MAKING A PRECONJUGATE

[75] Inventors: Chan S. Oh, Diamond Bar; Anthony K. Cheng, Brea; Josephine M. Michael, Placentia; Thomas S. Dobashi, Rosemead, all of Calif.

[73] Assignee: Beckman Instruments, Inc., Fullerton, Calif.

[*] Notice: The term of this patent shall not extend beyond the expiration date of Pat. Nos. 5,168,057, 5,196,351, and 5,422,281.

[21] Appl. No.: 797,384

[22] Filed: Feb. 7, 1997

Related U.S. Application Data

[63] Continuation of Ser. No. 357,782, Dec. 16, 1994, abandoned, which is a continuation of Ser. No. 899, Jan. 6, 1993, abandoned.

[51] Int. Cl.⁶ .................................................. G01N 33/53
[52] U.S. Cl. ...................... 436/501; 436/543; 436/547; 436/816; 436/817; 530/345; 530/403; 530/404; 530/405; 530/406; 530/408; 530/409; 530/410
[58] Field of Search ................... 530/345, 403, 530/404, 405, 406, 408, 409, 410; 436/501, 543, 547, 816, 817

[56] References Cited

U.S. PATENT DOCUMENTS

| | | | |
|---|---|---|---|
| 4,100,268 | 7/1978 | Scherr . | |
| 4,220,722 | 9/1980 | Rowley et al. | 435/188 |
| 4,243,749 | 1/1981 | Sadeh et al. | 435/7.92 |
| 4,328,311 | 5/1982 | Rowley et al. | 435/188 |
| 4,785,080 | 11/1988 | Farina et al. | 570/307 |
| 4,868,106 | 9/1989 | Ho et al. | 435/7.71 |
| 4,948,590 | 8/1990 | Hawrot et al. | 424/450 |
| 5,168,057 | 12/1992 | Oh et al. | 435/174 |
| 5,196,351 | 3/1993 | Harris et al. | 436/501 |
| 5,294,536 | 3/1994 | Palumko | 530/391.9 |

FOREIGN PATENT DOCUMENTS 0315317  5/1989  European Pat. Off. .

OTHER PUBLICATIONS

Khosravi et al (1991) Clin. Chem. 37/1;58–63.
Diamandis et al (1991) Clin. Chem. 37/5;625–636.
Liu et al (1979) Biochemistry (18)4;690–697.
Wilcheck et al (1988) Anal Biochem. 171;1–32.
Nelson et al (1989) Nucleic Acids Research 17(18);7187–7194.
Francina et al (1986) J. Immunol, Methods 87;267–272.
Redeuilh et al (1985) J. Biol Chem. 260(7);3996–4002.
Ashihara et al (1987) J. Clin. Lab, Anal. 1;80–82.

*Primary Examiner*—Ponnathapura Achutamurthy
*Assistant Examiner*—T. D. Wessendorf
*Attorney, Agent, or Firm*—William H. May; Margaret A. Kivinski

[57] ABSTRACT

A method for making a preconjugate which includes immunogenic species of a polymorphic analyte. The method is carried out by reacting an activated binding moiety, and a polymorphic analyte at room temperature for between about 10 hours and about 60 hours. The attaching reaction results in an excess of the preconjugate which includes the immunogenic species of the polymorphic analyte. The preconjugate can be used to make an immunoreactive conjugate useful as a developer antigen in a competitive inhibition immunoassay for the polymorphic analyte.

14 Claims, No Drawings

METHOD FOR MAKING A PRECONJUGATE

This application is a continuation of application Ser. No. 08/357,782 filed on Dec. 16, 1994, now abandoned, which is a continuation of application Ser. No. 08/000,899, filed Jan. 6, 1993, now abandoned.

BACKGROUND

We have invented a new method for making and using a preconjugate. In particular, our invention is directed to a method for making a preconjugate from a polymorphic analyte. The preconjugate can be used to make an immunoreactive conjugate.

There is a continuing and extensive need to detect and quantify various analytes in a test sample of a physiological fluid. An analyte can be a naturally occurring substance, such as an antibody, antigen or hormone or a metabolite or derivative thereof. An analyte can also be a man-made substance, such as a drug (including both therapeutic drugs and drugs of abuse) or a toxin or a metabolite or derivative thereof. The physiological fluid can be, for example, blood, serum, plasma, urine, amniotic, pleural or cerebrospinal fluid.

Immunoassay methods have shown considerable utility for the detection and quantification of various analytes. An immunoassay involves an immunoprecipitation reaction. An immunoprecipitation reaction can occur when two reaction partners, each with a specific binding affinity for the other, are combined in a suitable liquid medium. The reaction partners can be an antigen and a specific binding partner for the antigen, such as an antibody. Generally, one of the reaction partners is present in an unknown amount in the test sample of the physiological fluid, and is the analyte to be detected and/or quantified. Typically, the liquid medium is a buffered aqueous solution. Once initiated, the immunoprecipitation reaction results in the formation of immunoprecipitates, or antibody-antigen complexes that are usually insoluble, but which can also be soluble, in the liquid medium.

The presence of immunoprecipitates in the liquid medium can change optical properties, such as light scattering and light absorption properties of the liquid medium, by attenuation of incident light energy. These changes can be detected by an appropriate photometer in a photometric immunoassay. Photometric immunoassay techniques include both nephelometric and turbidimetric techniques.

In nephelometric immunoassay, a photometer is used to measure the reflection or scatter of light by the immunoprecipitates towards a light detector. The immunoprecipitates can be aggregates of an analyte and a specific binding partner for the analyte, or aggregates of an analyte-conjugate and the specific binding partner. The amount of light scattered by the immunoprecipitates is directly proportional to the number of immunoprecipitates present, which typically increases as the immunoprecipitation reaction proceeds. This proportionality permits a quantitative determination of analyte concentration.

In turbidimetric immunoassay, an attenuation or reduction of light energy passing through a liquid medium containing immunoprecipitates is measured by a light detector placed in the light path. The light energy reduction can be caused by reflection, scatter, and absorption of the incident light by the immunoprecipitates. The amount of light reduction caused by the immunoprecipitates is, again, directly proportional to the number of immunoprecipitates present, permitting a quantitative determination of analyte concentration.

Many analytes, including numerous drugs, are haptens. A hapten is a low molecular weight (typically weighing less than about 7,000 Daltons) substance that is generally incapable of causing, by itself, a significant production of antibodies upon administration to an animal body, including a human body. This can occur because a hapten is too small to be recognized by the body's immune system.

Traditional immunoassay methods for haptenic analytes are not practical because when a hapten-containing test sample is mixed with antibody, the hapten either does not combine with the antibody or does not form detectable immunoprecipitates. Fortunately, it is known that when a hapten is coupled to a larger, carrier molecule, the hapten can acquire antigenic properties. In other words, binding the hapten to the carrier molecule (to make an analyte-carrier molecule combination) permits the bound hapten to be recognized by an animal's immune system. Thus, an immunoprecipitation reaction can take place between the hapten (coupled to the carrier molecule), and an antibody to the hapten.

The analyte-carrier molecule combination can be called a conjugate or analyte conjugate. The terms conjugate and analyte conjugate are used herein to mean the same thing, a haptenic analyte joined to a carrier molecule. A conjugate that is able to participate in a immunochemical reaction with a specific binding partner for the analyte (or for an analyte analog), can be called an immunoreactive conjugate.

The ability of an immunoreactive conjugate to participate in an immunoprecipitation reaction has made possible the development of inhibition immunoassays (IIA) for diverse haptenic analytes in physiological fluids. As for immunoassays generally, an inhibition immunoassay is based on the principle that two specific binding partners, such as an antigen and its antibody, can engage in a specific affinity binding reaction to form a detectable aggregate.

Generally, an inhibition immunoassay is carried out by combining: (1) an immunoreactive conjugate comprising a haptenic analyte and a carrier molecule; (2) a specific binding partner for the haptenic analyte, and; (3) an aliquot of a test sample of a physiological fluid. The specific binding partner, typically an analyte antibody, does not discriminate between the free analyte (if any) in the test sample and the analyte portion of the immunoreactive conjugate, allowing the immunoreactive conjugate and the specific binding partner to combine to form a detectable aggregate.

The immunoreactive conjugate-specific binding partner aggregate can become detectable when it achieves a size large enough to affect optical properties of the liquid medium. Thus, large aggregates can attenuate transmission of incident light through the liquid medium. The amount of light attenuation by the liquid medium upon aggregate formation is inversely proportional to the amount of analyte present in the test sample. In this manner, an inhibition immunoassay can be used to detect and quantify various haptenic analytes in the test sample.

The immunoreactive conjugate used in the inhibition immunoassay is usually not made by combining the haptenic analyte directly to the carrier molecule. Typically, a spatial separation between the carrier molecule and the analyte is required to prevent the larger carrier molecule from unduly hindering recognition of the analyte by analyte antibody. Hence, a derivative of the analyte is prepared. This analyte derivative can be called a preconjugate. The preconjugate can be coupled to the carrier molecule to make the conjugate.

The preconjugate can comprise a binding moiety attached to an analyte of interest. The binding moiety in turn, can comprise a ligand and a spacer chain. Typically, the preconjugate is made by attaching the ligand and the analyte at opposite ends of the spacer chain. The spacer chain can reduce steric hindrance by the carrier molecule upon analyte antibody. Additionally, the spacer chain can enable the carrier molecule to undergo a specific affinity binding reaction with the ligand portion of the preconjugate, relatively unimpeded by the analyte portion of the preconjugate. Biotin:avidin are frequently used as ligand:carrier molecule binding partners.

Immunoreactive conjugates have been prepared for a variety of analytes. A method for making an immunoreactive conjugate must be able to produce conjugate that has a consistent immunoreactivity from assay to assay. Additionally, the method must be able to produce a yield of the desired immunoreactive conjugate sufficient for numerous and repetitive immunoassay procedures, as can be required in a clinical or hospital environment. In particular, therapeutic drug monitoring programs can require large amount of a consistently immunoreactive conjugate.

Unfortunately, a number of analytes have the characteristic of being polymorphic, that is of being comprised of both an immunogenic species and a nonimmunogenic species. Only the one or more immunogenic species of a polymorphic analyte can be used to make a useful immunoreactive conjugate. It can therefore be difficult to prepare a suitable immunoreactive conjugate from a polymorphic analyte. The immunogenic/nonimmunogenic species characteristic of a given polymorphic analyte may arise because such analytes have a plurality of isomeric forms and/or a plurality of reactive functional groups per analyte molecule.

Thus, upon attempting to make a preconjugate by reacting a binding moiety with a polymorphic analyte, a plurality of preconjugates can result. When these preconjugates are combined with a carrier molecule, a plurality of conjugates can result. Some of these conjugates may be immunoreactive. Other conjugates resulting from the addition of carrier molecule to the same preconjugate mixture may have little or no immunoreactivity or may exhibit a variable immunoreactivity.

Polymorphic analytes include various vitamins, such as vitamin $B_{12}$, steroids, antineoplastic and antibiotic compounds such as the aminoglycosides antibiotics, including gentamicin, tobramycin, and amikacin. Thus, gentamicin has A and C forms. Gentamicin A comprises a plurality of closely related or isomeric components, including at least gentamicin $A_1$, gentamicin $A_2$, gentamicin $A_3$, and gentamicin $A_4$. Gentamicin C comprises at least three closely related or isomeric components—gentamicin $C_1$, gentamicin $C_2$, and gentamicin $C_3$. It is possible that not all of the gentamicin isomers are immunologically active. If so, only the one or more immunologically active isomers of gentamicin (the immunogenic species) can be used to prepare an immunologically active gentamicin conjugate useful in a competitive inhibition immunoassay for test sample gentamicin.

Additionally, the aminoglycoside antibiotic tobramycin can have five or more reactive amine groups and four reactive hydroxyl groups per tobramycin molecule. Similarly, the aminoglycoside antibiotic amikacin can have four or more reactive amine groups and eight or reactive hydroxyl groups per amikacin molecule. As with gentamicin, the polymorphic characteristics of tobramicin and amikacin can result in a plurality of conjugates being formed, some of which will be immunoreactive while others may not be.

Various methods have been attempted to synthesize a significant yield of a suitable immunoreactive conjugate from a polymorphic analyte for use in a competitive inhibition immunoassay for the polymorphic analyte. These methods are generally inefficient and laborious.

Attempts have been made to separate out the useful immunoreactive species from the nonimmunoreactive species of a polymorphic analyte. The immunogenic species can then be used to make the immunoreactive conjugate. Such efforts have been largely unsuccessful or are difficult to achieve because of the structural and/or chemical similarity of the immunogenic and nonimmunogenic species of a particular polymorphic analyte.

Attempts have also been made to selectively block one or more of the reactive functional groups of the polymorphic analyte, on the theory that the remaining unblocked reactive functional groups of the polymorphic analyte will permit a higher yield of the desired immunoreactive conjugate. Such selective blocking procedures have proved to be impractical, time consuming, expensive and can still result in a low yield of the desired immunogenic species preconjugate.

A need therefore exists for a method of making a preconjugate from a polymorphic analyte that results in a high yield of preconjugate comprising an immunoreactive species of the polymorphic analyte.

SUMMARY

The present invention meets these needs. A method according to our invention results in a high yield of preconjugate comprising an immunogenic species of a polymorphic analyte.

The preconjugate comprising the immunogenic species of the polymorphic analyte can be used to make an immunoreactive conjugate. The immunoreactive conjugate can be used as a developer antigen in a competitive inhibition immunoassay for test sample polymorphic analyte.

DEFINITIONS

The following definitions of various terms are provided to facilitate an understanding of the present invention.

"Analyte" means the substance or group of substances to be detected and/or quantified in a physiological fluid. The term "analyte" encompasses analyte analog.

"Analyte analog" means a substance that can specifically bind to a reaction partner for the analyte in much the same manner as the analyte itself.

"Bidentate" or "bidentate conjugate" means a heterobifunctional conjugate with two chemical moieties, or bidentate members, attached by a spacer moiety, with each member being capable of specifically binding to a different macromolecule. Further definition and details regarding bidentate conjugates can be found in the U.S. Pat. No. 5,196,351, entitled "Bidentate Conjugate And Method Of Use Thereof", issued Mar. 23, 1993.

"Binding moiety" means a ligand joined to a spacer compound.

"Carrier molecule" means a compound that has a specific binding affinity for the ligand portion of the binding moiety.

"Polymorphic analyte" means an analyte that has one or more isomers and/or more reactive functional groups per molecule of the analyte such that the polymorphic analyte comprises both an immunogenic species and a nonimmunogenic species.

"Hapten" means a partial or incomplete antigen, typically a low molecular weight drug, that is generally incapable of causing by itself a significant production of antibodies.

"Immunogenic species" means: (1) the isomer or isomers of a polymorphic analyte that can be used to make a preconjugate useful for making an immunoreactive conjugate, and/or; (2) the polymorphic analyte molecule or molecules with a plurality of functional groups that can be used to make an preconjugate useful for making an immunoreactive conjugate.

"Ligand" means a molecule having a specific binding affinity for a carrier molecule.

"Nonimmunogenic species" means: (1) the isomer or isomers of a polymorphic analyte that can be used to make a preconjugate, which preconjugate when used to make a conjugate, results in a conjugate that is less immunoreactive than the conjugate made from a preconjugate comprising an immunoreactive species of the polymorphic analyte, and/or; (2) the polymorphic analyte molecule or molecules with a plurality of functional groups that can be used to make an preconjugate which preconjugate when used to make a conjugate, results in a conjugate that is less immunoreactive than the conjugate made from a preconjugate comprising an immunoreactive species of the polymorphic analyte.

"Polymorphic analyte" means an analyte that has one or more isomers and/or more reactive functional groups per molecule of the analyte such that the polymorphic analyte comprises both an immunogenic species and a nonimmunogenic species.

"Spacer compound" means a substance attached to or capable of being attached simultaneously to both a ligand and a polymorphic analyte.

A method according to the present invention for making a preconjugate from a polymorphic analyte can have two steps. The first step is to react in an attaching reaction a binding moiety and a polymorphic analyte. The polymorphic analyte comprises an immunogenic species and a nonimmunogenic species. The second step is to separate the preconjugate comprising the immunogenic species of the polymorphic analyte from the preconjugate comprising the nonimmunogenic species of the polymorphic analyte.

The attaching reaction can result in a stoichiometric excess of the preconjugate comprising the immunogenic species of the polymorphic analyte relative to the amount of the preconjugate comprising the nonimmunogenic species of the polymorphic analyte.

Preferably, the attaching reaction takes place in a reaction medium comprising a liquid capable of solubilizing the binding moiety and the polymorphic analyte.

Also within the scope of the present invention is (1) a product by the process of the disclosed method and (2) an immunoreactive conjugate made from the preconjugate prepared by the attaching reaction. Such an immunoreactive conjugate can be made by contacting the preconjugate comprising the immunogenic species of the polymorphic analyte with a carrier molecule.

The disclosed method can be used to make preconjugates useful for the preparation of immunoreactive conjugates from many different polymorphic analytes.

DESCRIPTION

We have discovered that under certain reaction conditions a binding moiety and a polymorphic analyte can be combined to consistently obtain a high-yield synthesis of a useful preconjugate. The preconjugate can be combined with a carrier molecule to make an immunoreactive conjugate. The immunoreactive conjugate can be used as a developer antigen in a competitive inhibition immunoassay for the polymorphic analyte.

A method according to the present invention commences by reacting in an attaching reaction, a binding moiety and a polymorphic analyte. Preferably, the attaching reaction is carried out in a reaction medium that is capable of solubilizing both the binding moiety and the polymorphic analyte at all the concentrations of these reactants set forth herein.

The second step of the method is to separate the preconjugate comprising the immunogenic species of the polymorphic analyte from the preconjugate comprising the nonimmunogenic species of the polymorphic analyte. The separation step removes substantially all of the preconjugate comprising the nonimmunogenic species of the polymorphic analyte from contact with the preconjugate comprising the immunogenic species of the polymorphic analyte. Thus, the separation step can yield essentially pure preconjugate comprising the immunogenic species and useful for making an immunoreactive conjugate. The preconjugate comprising the immunogenic species of the polymorphic analyte can be contacted with a carrier molecule to make the immunoreactive conjugate.

The polymorphic analyte used to prepare the preconjugate, comprises at least one immunogenic species and at least one nonimmunogenic species. Thus, the polymorphic analyte has a plurality of isomeric forms and/or a plurality of reactive functional groups per analyte molecule.

The polymorphic analyte can be selected from the group consisting of gentamicin, tobramycin, amikacin, vitamin $B_{12}$, netilmicin, sisomycin, kanamycin, neomycin, vancomycin, erythromycin (including erythromycin A, B, C, E, F, N-demethylerythromycin A and the corresponding propionate esters), bleomycin, capreomycin, dactinomycin, lincomycin, oleandomycin, and derivatives, metabolites, and analogues thereof.

The attaching reaction can result in a stoichiometric excess of preconjugate comprising the immunogenic species of the polymorphic analyte relative to the amount of preconjugate comprising the nonimmunogenic species of the polymorphic analyte.

Preferably, the ratio of the stoichiometric excess of the preconjugate comprising the immunogenic species of the polymorphic analyte to the preconjugate comprising the nonimmunogenic species of the polymorphic analyte resulting from the attaching reaction is at least about 2:1. We have found that by our method it is possible to obtain such a ratio of about 3:1, 4:1 or 5:1. In a particularly preferred embodiment of the present invention, the ratio of the stoichiometric excess of the preconjugate comprising the immunogenic species of the polymorphic analyte to the preconjugate comprising the nonimmunogenic species of the polymorphic analyte resulting from the attaching reaction can be about 9:1. These ratios were determined by, for example, visual examination of the relative sizes of the thin layer chromatography (TLC) spots of the attaching reaction products.

The attaching reaction is preferably carried out at a temperature of at least about 10° C. At a temperature below about 10° C., the attaching reaction takes much longer to go to completion. More preferably, the attaching reaction is carried out at a temperature between about 15° C. and about 30° C. Above about 30° C. the reactants can begin to decompose.

Additionally, the attaching reaction is preferably carried out for at least about 8 hours, and more preferably for between about 10 hours and about 60 hours to ensure that the reaction has run essentially to completion.

Preferably, the molar ratio of polymorphic analyte to binding moiety present at the beginning of the attaching reaction is at least about 0.5:1. More preferably, this ratio is between about 0.5:1 and about 30:1, and most preferably between about 0.5:1 and about 5:1. In a particularly preferred embodiment, this ratio can be between about 1:1 and about 3:1. At a ratio of less than about 0.5:1 insufficient analyte is present to react efficiently with the binding moiety. When the ratio is above about 30:1, the additional polymorphic analyte has an insignificant effect on the desired preconjugate yield. As these ratios approach equimolar ratios, the yield of the desired preconjugate can increase. Additionally, when the indicated molar ratios as used, the desired preconjugate can be obtained while conserving expensive reagents. Furthermore, the particular molar ratios specified has been found to result in immunoreactive conjugates with more reproducible and predictable immunoreactivity characteristics.

The method can also include the step of activating the binding moiety in an activating reaction prior to the attaching reaction by mixing the binding moiety with a coupling reagent capable of attaching to and activating the binding moiety. When this step is carried out, the molar ratio of the binding moiety to the coupling reagent present at the beginning of the activating reaction is preferably at least about 1:0.9, and more preferably between about 1:1 and about 1:5. These molar ratios have been found to provide sufficient activated binding moiety for the attaching reaction step. When the ratio is greater than about 1:5, an excessive amount of coupling reagent which does not significantly contribute to binding moiety activation is in use. Most preferably, an excess of coupling agent over the binding moiety analyte of at least about 20% can be used to facilitate activating essentially all the binding moiety with an effective amount of the coupling reagent.

A more detailed method for making a preconjugate comprising a binding moiety and an immunogenic species of a polymorphic analyte bound to the binding moiety, preferably has the steps of firstly activating a binding moiety by mixing the binding moiety with a coupling reagent capable of attaching to and activating the binding moiety. The next step is to react in an attaching reaction at a temperature between about 15° C. and about 30° C., for between about 10 hours and about 60 hours, the activated binding moiety and the polymorphic analyte comprising an immunogenic species and a nonimmunogenic species. The molar ratio of the polymorphic analyte to the activated binding moiety can be between about 0.5:1 and about 30:1, and the molar ratio of the polymorphic analyte used in the attaching reaction to the coupling reagent used to activate the binding moiety can be between about 1:1 to about 1:5. The final step is separating preconjugate comprising the immunogenic species of the polymorphic analyte from preconjugate comprising the nonimmunogenic species.

A method for making an aminoglycoside preconjugate, preferably has the steps of first activating a binding moiety in an activating reaction by mixing the binding moiety with a coupling reagent capable of attaching to and activating the binding moiety. The second step is to react in the attaching reaction at a temperature between about 15° C. and about 30° C., for between about 10 hours and about 60 hours, the activated binding moiety and the polymorphic aminoglycoside. The polymorphic aminoglycoside comprises at least one immunogenic species and at least one nonimmunogenic species. The attaching reaction can result in a stoichiometric excess of the preconjugate comprising the immunogenic species of the polymorphic aminoglycoside. The molar ratio of the polymorphic aminoglycoside to the activated binding moiety can be between about 0.5:1 and about 30:1; the molar ratio of the binding moiety to the coupling reagent present at the beginning of the activating reaction can be between about 1:1 to about 1:5. The final step of the method is to separate the preconjugate comprising the immunogenic species of the polymorphic aminoglycoside from preconjugate comprising the nonimmunogenic species of the polymorphic aminoglycoside. The separation step removes substantially all of the preconjugate comprising the nonimmunogenic species of the polymorphic aminoglycoside from contact with the preconjugate comprising the immunogenic species of the polymorphic aminoglycoside. Thus, the separation step can yield essentially pure aminoglycoside preconjugate comprising the immunogenic species and useful for making an immunoreactive conjugate. The preconjugate comprising the immunogenic species of the polymorphic analyte can be contacted with a carrier molecule to make the immunoreactive conjugate.

A suitable binding moiety can be made by joining a ligand to a spacer compound in a joining reaction. The ligand can be any small molecule (molecular weight less than about 7,000 Daltons) that is capable of undergoing a specific binding reaction with the carrier molecule. The ligand is a compound that is not identical to the analyte so that the analyte and the ligand have different specific binding partners. Thus, the ligand can be biotin, a hormone such as insulin, a steroid hormone, a thyroid hormone, a polypeptide, an oligonucleotide, a vitamin such as $B_{12}$, or folic acid, a hapten such as 1-substituted-2, 4-dinitrobenzene (also known as dinitrophenol, or DNP), digoxin or fluorescein.

The carrier molecule is typically a large molecule (molecular weight greater than about 7,000 daltons) capable of undergoing a specific affinity binding reaction with the ligand. The carrier molecule can be a natural or synthetic macromolecule such as an antibody, avidin, an intrinsic factor, a lectin, or a complementary oligonucleotide. A preferred ligand-carrier molecule combination is biotin-avidin because of the ready available of these compounds and their suitability for use in the disclosed method.

The spacer compound is interposed between an polymorphic analyte and the ligand, serving to spatially separate the analyte from the ligand. The spacer compound thereby functions to allow both the analyte and the ligand to simultaneously bind to their respective specific binding partners. Thus, the spacer compound connects the analyte to the ligand and regulates the ability of the analyte and ligand members of the preconjugate to simultaneously bind to their respective binding partners. Details regarding minimum, maximum, and preferred spacer compound lengths so as to enable simultaneous binding of two specific binding can be found in the copending U.S. patent application entitled "Novel Bidentate Conjugate and Method of Use Thereof", Ser. No. 07/536,058, filed Jun. 8, 1990, "(now U.S. Pat. No. 5,196,351, issued Mar. 23, 1993)", which application is incorporated herein in its entirety.

Because the polymorphic analyte and the ligand portions of the preconjugate have different specific binding partners, the preconjugate can be referred to as a heterobifunctional preconjugate.

Preferably, the binding moiety is activated by a coupling reagent prior to being reacted with the polymorphic analyte in the attaching reaction. An activated binding moiety can react more readily with the polymorphic analyte. The coupling reagent is preferably a dehydrating agent such as for example, carbonyldiimidazole (CDI), 1-ethyl-3-C3-dimethyl amino propyl(carbodiimide) (EDAC), dicyclohexylcarbodiimide (CPCC), or various suitable and known to the art phosphate compounds.

The reaction medium can be a liquid capable of solubilizing the activated binding moiety, the polymorphic analyte, and the coupling reagent. In particular, an ability of the reaction medium to solubilize the binding moiety is an important characteristic of a suitable reaction medium. Suitable reaction media can include dimethylformamide, water, dimethysulfoxide, and various mixtures thereof.

Where the polymorphic analyte selected is the aminoglycoside antibiotic amikacin, preferably the reaction medium contains a carbonate compound. Addition of a carbonate compound to the reaction medium was found to considerably facilitate work-up of the reaction products and isolation of the desired immunoreactive species amikacin preconjugate from other reaction products such as the nonimmunoreactive species amikacin preconjugate. More preferably the carbonate is a bicarbonate because a bicarbonate was found to be more effective than a carbonate. Most preferably, the carbonate is an alkali metal bicarbonate, such as sodium bicarbonate because such compounds are inexpensive, readily available, and have been found to assist isolation of the immunoreactive species amikacin preconjugate reaction product.

Additionally, where the polymorphic analyte selected is the aminoglycoside antibiotic amikacin, we have found that a stoichiometric excess of preconjugate comprising the immunogenic species of the amikacin relative to the amount of preconjugate comprising the nonimmunogenic species of the amikacin is not generally obtained.

The immunoreactive conjugate prepared from the preconjugate can be used as a developer antigen in a competitive inhibition immunoassay for a polymorphic analyte of interest. The immunoassay can be a photometric immunoassay such as, for example, a nephelometric or turbidimetric competitive inhibition immunoassay method. The consistent immunoreactivity of the conjugates prepared from the disclosed preconjugates were determined by standard competitive immunoassay procedures as set forth by the following examples.

EXAMPLES

The following examples set forth illustrations of various features and embodiments of the present invention and are not intended to limit the scope of the claimed invention. In these Examples, all the preconjugates prepared were bidentate conjugates.

Example 1

(Preparation of benzyloxycarbonyl-6-aminohexanoic acid)

Benzyloxycarbonyl-6-aminohexanoic acid used to make benzyloxycarbonyl-bis-6-amino hexanoic acid was prepared as follows. To a flask there was added a stir bar, 77.2 g (0.59M) of aminocaproic acid (98% pure, formula weight (FW) 131.18, melting point (MP) 210, freezing point (FP) 36° C.) (Aldrich Chemical Co.) in 160 mL of water, and 90 mL of 6N sodium hydroxide. The solution was cooled in an ice bath to about 5° C. and maintained at that temperature while being stirred for the following steps. To the flask there was then added over 90 minutes, 84 mL (100 g, 0.586 mM) of benzylchloroformate (95%, FW 170.60, FP 91° C., density (d) 1.195, and n 1.5190) (Aldrich Chemical Co.) and 295 mL of 2N sodium hydroxide. The benzylchloroformate in sodium hydroxide mixture was added to the flask in 10 equal portions of 8.5 mL of the benzylchloroformate followed by 29 mL of the sodium hydroxide.

After addition of the tenth portion of 8.5 mL of the benzylchloroformate and 29 mL of the sodium hydroxide, the solution was stirred for one hour, then brought to room temperature and stirred for one more hour. A white solution with a pH of 9 was thereby formed. The solution was then poured into a 1 L beaker containing 200 g of ice. The pH of the solution was adjusted to pH 2 with 50 mL of concentrated hydrochloric acid (HCL). Sufficient water was then added so that the resulting solid white precipitate mass could be stirred, and the pH was brought back to pH 2 with HCL. The white precipitate was filtered and washed with acidified water. The liquid filtrate was then acidified to precipitate additional white precipitate.

The white precipitate was then resuspended in 1500 ml of water and triturated to break up lumps, followed by being stirred for 15 hours at room temperature. The white precipitate was then filtered, washed with 1.0 L of water, and compressed on a Buchner funnel using the bottom of a 50 mL erlenmeyer flask. The white solid precipitate was then washed with 200 mL, 100 mL, and 100 mL portions of hexane to remove water and benzylchloroformate, and then was dried. There was obtained 134.5 g (0.51M, 86% yield) of a white solid (mp 57.5°–59° C.), benzyloxycarbonyl-6-aminohexanoic acid.

Example 2

(Preparation of benzyloxycarbonyl-bis-6-aminohexanoic acid)

Benzyloxycarbonyl-bis-6-aminohexanoic acid used to make benzyloxycarbonyl-tris-6-amino hexanoic acid was prepared as follows. Fifty-one point five grams (51.5 g) (0.196M) of benzyloxycarbonyl-6-aminohexanoic acid (FW 265.95) obtained following the procedure set forth in Example 1, was dissolved in 640 mL of toluene (ACS grade) and 20 mL (0.143M) of triethylamine (FW 101.19, BP 88.8° C., FP 20° C., d 0.726) (Aldrich Chemical CO.). The solution was then cooled to 0° C. in an ice bath. While stirring the cold solution, 21 mL (23.8 g, 0.219M) of ethyl chloroformate (FW 108.52, BP 93° C., FP 36° C., d 1.135) (Aldrich Chemical Co.) was added dropwise. The solution was then stirred for an additional 30 minutes, before being filtered to remove a white solid precipitate, triethylamine hydrochloride.

To the filtered solution, cooled in the ice water bath, there was added over 45 minutes while stirring, 25.4 g (0.194M) of aminocaproic acid dissolved in 100 mL of cold 2N sodium hydroxide. The solution was then stirred for 1 hour at 0° C., followed by being stirred for 2 hours at room temperature during which a white precipitate formed. The solution was then allowed to stand overnight at room temperature before decanting the toluene from the white solid precipitate.

The white solid precipitate was then washed with 3 lots of 100 mL of ethyl ether. The white solid was then filtered and placed in acidic water pH 2, followed by being filtered, washed with hexane and dried to obtain 31 g (0.0818 mM, 41% yield, melting point 102°–103° C.) of a white solid, benzyloxycarbonyl-bis-6-aminohexanoic acid (FW 379.13). Silica gel thin layer chromatography of the white solid in 9/1 chloroform/methanol gave a single spot, Rf 0.45.

Example 3

(Preparation of benzyloxycarbonyl-tris-6-aminohexanoic acid

Benzyloxycarbonyl-tris-6-amino hexanoic acid used to make tris aminohexanoic acid was prepared as follows. Into a 500 mL round bottom flask there was placed 24 g (63.4 mM) of benzyloxycarbonyl-bis-6-aminohexanoic acid (FW 378.47) obtained by following the procedure of Example 2, a stir bar, 200 mL of dry tetrahydrofuran (THF) (FW 72.11, boiling point (BP) 67° C., and density (d) 0.985) (Aldrich Chemical Co.), 60 mL of dry dimethylformamide (DMF), and 9 mL (6.534 g, 64.69 mM) of triethylamine (FW 101.19, BP 89° C., d 0.726) (Aldrich Chemical Co.)

A drying tube was attached, the mixture was stirred to dissolve the solids, and then placed in a salt/ice bath to cool to −5° C. Six mL (6.810 g, 62.75 mM) of ethyl chloroformate (FW 108.52, BP 93° C., d 1.135) (Aldrich Chemical Co.) was then added to the flask, stirred and the mixture was allowed to incubate for 15 minutes at −5° C. The mixture was then filtered, and to the filtrate there was added over a period of 15 minutes, 16.6 g (126.54 mM) of aminocaproic acid (FW 131.18, MP 210° C.) (Aldrich Chemical Co.), dissolved in 69 mL of 2N cold sodium hydroxide. The mixture was then stirred for 15 minutes at −5° C., followed by being stirred for another 15 minutes at room temperature. The solvent was then removed completely by rotary evaporation.

The remaining solid was transferred using water to a beaker and acidified to pH 2 using concentrated HCL to obtain a white solid. This solid was filtered and washed with water. While the solid was wet, it was recrystallized from methanol, and cooled overnight at 4° C. The solid was then filtered and dried to obtain 17.54 g (58% yield) of a white solid, benzyloxycarbonyl-tris-6-aminohexanoic acid. Silica gel thin layer chromatography was used to confirm the presence of the single end product.

Example 4

(Preparation of Tris Aminohexanoic Acid)

Tris aminohexanoic acid used to make biotin hexanoic acid was prepared as follows. Three grams (6.1 mM) of benzyloxycarbonyl-tris-6-amino hexanoic acid (FW 491.6), obtained by following the procedure of Example 3, was dissolved in 150 mL of methanol in a 500 mL round bottom flask with a stir bar. The flask was then flushed with nitrogen. Two spatulas full or about one half gram of 5% palladium catalyst on activated charcoal (Kodak or Aldrich Chemical Co.) was then added to the flask. The flask was then flushed with hydrogen gas at atmospheric pressure and room pressure. After being stirred for 3.5 hours, a silica gel thin layer chromatograph, in 8/2 chloroform/methanol, was prepared and visualized with UV, iodine, and ninhydrin spray. The TLC showed disappearance of the starting material benzyloxycarbonyl-tris-6-amino hexanoic acid (Rf 0.6), and appearance of the amine product.

After being stirred for a total of 4 hours, the solution in the flask was flushed with nitrogen, heated to a temperature sufficient to dissolve the solids, and then filtered through a Whatman #1 filter (Whatman Co.) with diatomaceous earth to remove the palladium catalyst. The solution was then concentrated by rotary evaporation to 30 mL and combined with 30 mL of ethyl ether until the solution become cloudy and was placed in a cold room at 4° C. overnight. Silica gel thin layer chromatography, in 1/1 chloroform/methanol with 4% ammonium hydroxide, and visualized with iodine and ninhydrin spray. The TLC gave a single spot, Rf 0.3. The solution was then filtered to obtain 2.1 g (5.39 mM) (89% yield) of a white solid, tris aminohexanoic acid (FW 389.6).

Example 5

(Preparation of Biotin Tris-Amino-Hexanoic Acid)

A biotin hexanoic acid derivative capable of being covalently linked to an aminoglycoside analyte, such as gentamicin, was synthesized and purified as follows. Into a round bottom flask there was placed 1252 mg (5.13 mM) of biotin (FW 244) and 60 mL of DMF with a magnetic stir bar. A drying tube was attached and the flask was heated in an oil bath for 15 minutes at a temperature between 70° and 75° C. To the flask there was then added 923 mg (5.70 mM) of 1,1'-carbonyldiimidazole (CDI) (FW 162), followed by stirring and incubation for 30 minutes at a temperature between 70° and 75° C.

The reaction mixture was then cooled to room temperature before adding 656 mg (5.70 mM) of N-hydroxysuccinimide (NHS) (FW 115) to the flask. The mixture was then stirred for 18 hours at room temperature to obtain an activated biotin solution. Two grams (5.13 mM) of tris-aminohexanoic acid (FW 389.6), obtained by following the procedure of Example 4, was then dissolved in 60 ml of 0.2M sodium bicarbonate and added to the activated biotin solution. Besides tris-aminohexanoic acid, many longer or shorter chain organic acids can be prepared and used depending upon the desired steric distancing of an analyte from a carrier molecule in the final analyte-conjugate.

The reaction was then allowed to proceed overnight, followed by adjustment of the reaction mixture to pH 2 by addition of 6M HCL and filtration of the solid reaction product to remove fluid. The solid obtained was triturated with 100 mL of 0.6N HCL, filtered, recrystallized from methanol and dried to obtain 2.8 g (89% yield) of a white solid, biotin tris-hexanoic acid (FW 615). Biotin tris-hexanoic acid is a binding moiety useful for making a preconjugate according to the method set forth in detail below. This particular binding moiety has an 18 carbon atom spacer chain.

Silica gel thin layer chromatography, in 8/2 chloroform/methanol and visualized with iodine and ninhydrin spray, was used at various stages of the synthesis to show disappearance of the starting amine and appearance of the biotin acid derivative.

Example 6

(Preparation of a Biotinylated Gentamicin Preconjugate)

A. A gentamicin-biotin preconjugate capable of undergoing a specific affinity binding reaction with avidin was prepared as follows. The abbreviation "mM" as used in this and in other Examples means millimole or one thousandth of a mole. Into a 25 mL round bottom flask there was placed 100 mg (0.172 mM) of the biotin tris aminohexanoic acid binding moiety prepared by following the procedure of Example 5, dissolved in 15 mL of DMF (anhydrous 99%+, gold label, FW 73.10, BP 153° C., d 0.945) (Aldrich) by application of heat. The reaction flask was then placed in an oil bath at 70° to 75° C. for 15 minutes. There was then added to the flask 30 mg (0.185 mM) of 1,1'carbonyldiimidazole (CDI) (MW 162.2) (Sigma Chemical Co.), as the coupling reagent to activate the binding moiety. The temperature of the reaction solution was maintained at 70° to 75° C. for 30 minutes, followed by being cooled to room temperature.

To the reaction flask there was then added 20 mg (0.172 mM) of N-hydrosuccinimide (NHS) (97%, FW 115.09) (Aldrich), followed by stirring overnight at room temperature. The next step in the synthesis was dissolve 71 mg (0.0855 mM) of gentamicin sulfate, potency: 591 μg gentamicin per mg of gentamicin sulfate, 9.4% water) (Sigma) in 3 mL of water in a test tube. One hundred milligrams of sodium bicarbonate (FW 84.01) (Mallinckrodt) was then slowly added to the gentamicin sulfate/water solution in the tube. After the bubbling stopped, another 100 mg of sodium bicarbonate was added to the gentamicin solution in the tube.

The gentamicin solution was then added to the activated biotin in the reaction flask to initiate an attaching reaction between the activated binding moiety and the gentamicin. Eight mL of water in 1 mL increments was then added to the reaction flask until the reaction solution became clear. The reaction solution was then stirred for 15 hours at room temperature. In another experiment the reaction solution was stirred at room temperature for 60 hours with equivalent results. The reaction solution was then evaporated to dryness and the remaining white residue was triturated with methanol and filtered.

The filtrate was evaporated to dryness and the remaining solid residue was dissolved in 5 mL of methanol, followed by placement on a 1 cm by 30 cm column chromatography column of cellulose packed as a methanol slurry. The column was then eluted with 75 mL of methanol, followed by 100 mL of methanol/5% ammonium hydroxide, followed by 100 mL methanol/10% ammonium hydroxide. Progress of the column was followed by TLC of column elution fractions in methanol. Selected fractions were pooled, and evaporated to dryness to obtain 14.5 mg of a gentamicin-biotin preconjugate ready for conjugation to avidin.

The molar ratio of gentamicin (polymorphic analyte) to biotin tris aminohexanoic acid (binding moiety) to CDI (coupling reagent) to NHS (the G:B:CDI:NHS ratio) at the beginning of the attaching reaction to form the preconjugate was 1:2:2.2:2.

B. A second gentamicin-biotin preconjugate capable of undergoing a specific affinity binding reaction with avidin was prepared as follows. The relative molar ratios of gentamicin:biotin (or biotin tris aminohexanoic acid):CDI used were 29:1:1.2. Ten milligrams (0.017 mM) of biotin tris aminohexanoic acid was dissolved in 10 mL of DMF as the reaction medium, by being warmed in an oil bath at 70° C. for 10 minutes. This was followed by addition of 3.5 mg (0.0216 mM) of CDI (MW 162) as the coupling reagent and, stirring in the oil bath for 30 minutes, and then by being stirred at room temperature for 1 hour. NHS (2.5 mg, 0.0217 mM, MW 115) was then added and the reaction mixture was stirred overnight. The next step was to slowly add 234 mg (0.50 mM) of gentamicin (MW 462) in 20 mL of dry DMF, to the reaction mixture followed by stirring overnight. The solvent was then evaporated.

The remaining solid residue was dissolved in a minimum amount of methanol and loaded onto a silica gel column, 1 cm by 30 cm packed with 7 g of silica gel. Methanol followed by 10% ammonium hydroxide/methanol was used as the eluent, to obtain 0.134 g of a second preconjugate.

C. A third gentamicin-biotin preconjugate capable of undergoing a specific affinity binding reaction with avidin was prepared as follows. The relative molar ratios of gentamicin:biotin (or biotin tris aminohexanoic acid):CDI used were 1.3:1:1.2. To a round bottom flask equipped with a drying tube there was added 2 g (3.44 mM) of biotin tris aminohexanoic acid dissolved in 150 ml of dry DMF. The flask was then placed in an oil bath at 70° to 75° C. for 15 minutes. As coupling reagent, 667 mg (4.12 mM) of CDI was added, followed by stirring at 75° C. for 30 minutes.

After cooling to room temperature, 470 mg (4.10 mM) of NHS was added to the flask, and the reaction was allowed to proceed for 20 hours. Gentamicin in an amount of 2.134 g (4.16 mM) was then dissolved in 100 mL of dry DMF. The activated biotin was then added through a separating funnel to the gentamicin/DMF solution over a period of 30 minutes. This was followed by stirring for 24 hours at room temperature.

After evaporation of the solvent under reduced pressure, the residue was dissolved in a small quantity of methanol, and loaded onto the top of a 2.5 cm by 60 cm column containing 70 g of silica gel packed as a methanol slurry. The excess, unreacted biotin was eluted using 1400 mL of methanol. The column was then eluted with 5% ammonium hydroxide in methanol. Column fractions were monitored using TLC (5% $NH_4OH/CH_3OH$). Fractions exhibiting a positive reaction to cinnamaldehyde spray were pooled to give 1.5 g of a third gentamicin-biotin preconjugate.

For all the gentamicin-biotin preconjugates prepared as set forth above, it was clear that the reaction between the activated biotin ester and the gentamicin resulted in an excess of the amount of the gentamicin preconjugate that could be used to make an immunoreactive gentamicin conjugate (i.e. biotin binding moiety joined to an immunoreactive species of the gentamicin), as compared to the amount of gentamicin preconjugate that could not be used to make an immunoreactive gentamicin conjugate (i.e. biotin binding moiety joined to a nonimmunoreactive species of the gentamicin).

Thus, for example, a visual inspection of the relative size of the TLC reaction product spots, showed that the spot of immunoreactive gentamicin species preconjugate was larger than the TLC spot of the nonimmunoreactive gentamicin species preconjugate. Examination of the relative size of the TLC spots (followed by conjugation with avidin of at least the major product (large TLC spot) and subsequent immunoreactivity study) showed that the yield of the desired preconjugate was in excess as compared to the yield of the undesired preconjugate. Specifically, for the reaction parameters specified the relative area of the immunoreactive gentamicin species preconjugate TLC spot:nonimmunoreactive gentamicin species preconjugate TLC spot varied from about 2:1 to about 5:1.

Gentamicin:biotin ratios of 5:1, 10:1, 15:1. 20:1, 25:1, and various intermediate concentration ratios can be used in the method set forth above. It can be reasonably expected that the reaction products obtained by such alternate analyte:binding moiety ratios would yield preconjugates that could be used to make immunoreactive conjugates.

Additionally, the gentamicin (polymorphic analyte):CDI (coupling reagent) ratios can, it is reasonably postulated, be varied to any ratio between about 0.5:1 and about 30:1 with results comparable to those set forth above.

Example 7

(Preparation of Gentamicin-Biotin-Avidin Conjugates)

I. A gentamicin-biotin-avidin conjugate useful as an inhibitor in competitive inhibition immunoassays for gentamicin was prepared as follows. Into a 50 mL tube there was placed 203.1 mg of avidin dissolved in 20 mL of 0.1M phosphate buffer, pH 7.4, with 100 $\mu$L of HABA. Next, 21 mg of the preconjugate made by following the procedure of Example 6A. above, in methanol, was added to the avidin solution in 200 $\mu$L aliquots (the color changed from pink-orange to light yellow), and allowed to stand for 1 hour. The mixture was then transferred to a dialysis bag (6.4 mm, 12,000–14,0000 MW cutoff) using 1 mL of citrate buffered saline (CBS), pH 6.0. Dialysis was carried out at 4° C. in CBS, pH 6.0 at a volume of 2000 mL, with 5 changes over 3 days to recover 29 mL of an immunoreactive gentamicin-($C_{18}$,$N_3$)-biotin-avidin conjugate.

II. A second gentamicin-biotin-avidin conjugate was prepared by dissolving 0.134 of the preconjugate made by following the procedure of Example 6B. above in 5 ml of methanol. Twenty milligrams of avidin (Boehringer Manhein GmbH) was then dissolved in 1 mL of phosphate buffer, 0.1M, pH 7.4, with 20 μL of 2-(4 hydroxyphenylazo) benzoic acid indicator. The preconjugate solution was then added to the avidin solution in 50 μL portions, until 450 μL had been added. The color changed from pink-orange to light yellow. The mixture was then left at room temperature for 1 hour, followed by dialysis against 500 mL of 0.05M phosphate buffer, pH 7.4. Four changes of the buffer were made over a two day period, as the dialysis continued.

III. A third gentamicin-biotin-avidin conjugate was prepared by dissolving 1.4 g of the preconjugate made by following the procedure of Example 6C. above in 10 ml of methanol. One hundred milligrams of avidin (Boehringer) was then dissolved in 5 mL of phosphate buffer, 0.1M, pH 7.4, followed by addition of 100 μL of 2-(4 hydroxyphenylazo) benzoic acid indicator. A 100 μL portion, followed by a 50 μL portion of the preconjugate solution was then added to the avidin solution. Five mL of the phosphate buffer was then added, followed by being left at room temperature for 1 hour. The mixture was then left at room temperature for 1 hour, followed by dialysis against 500 mL of 0.05M phosphate buffer, pH 7.4. Four changes of the buffer were made over a two day period, as the dialysis continued.

Example 8

(Preparation of Monoclonal Antibodies to Gentamicin)

Hybridomas capable of making monoclonal antibody to two forms or species of gentamicin were prepared. The materials used were as follows. The myeloma cells used were derived from the P3X63-Ag8.653 myeloma line, a non-secreting mouse myeloma line developed by Kearney et al., *J. Immunol.*, 123:1548 (1979). The spleen cells used were taken from Balb/c mice immunized by the procedure below. The growth media was DME low glucose (Irvine Scientific), supplemented with 10% fetal calf serum (Hyclone), and 2 mM 1-glutamine (Irvine Scientific). The used media was growth media from a three day culture of 653.1 cells, centrifuged and filtered to remove cells. The CHAT Media was 50% growth media and 50% conditioned media with 100 units/ml of penicillin-streptomycin solution (irvine Scientific), $4 \times 10^{-7}$M aminopterin (Sigma), $1 \times 10^{-4}$M hypoxanthine (MA Bioproducts), $1.6 \times 10^{-5}$M thymidine (MA Bioproducts), and 10 units/ml insulin (Eli Lily). The conditioned media was 50% growth media-50% used media and $2.5 \times 10^{-5}$M b-mercaptoethanol (Sigma). Polyethylene glycol (PEG) with a molecular weight between about 1300 and 1600 (Sigma) was used. The injection media was DME low glucose with 100 units/ml penicillin-streptomycin solution. One-half milliliter of Pristane (2,6,10,14-tetramethylpentadecane, available from Aldrich) was injected intraperitoneally into each Balb/c mouse two weeks prior to hybridoma injection.

The hybridomas were made using the method developed by Kohler and Milstein, *Nature* 256:495 (1975). The spleen from the immunized mouse was aseptically removed after cervical dislocation and was ground in a tissue sieve until a single-cell suspension was obtained. After washing, the cells were mixed with the washed 653.1 myeloma cells in a 2:1 ratio of spleen to myeloma cells and then pelleted. The supernatant was removed and the PEG added slowly over one minute. PBS was added to bring the total volume to 22 ml and the cells were then pelleted for 8 minutes after the start of PEG addition. The pellet was resuspended in 200 ml of CHAT media and 0.2 ml of the suspension was added to each well of ten 96-well microtiter plates. The wells were supplied with fresh CHAT on days 6 and 7 post fusion.

Testing of the wells for growth using radioimmunoassay (RIA) began on day 10 and continued over the next 3–4 days. Wells with a count greater than the negative control were retested on the following day. If the reading remained greater than the negative control on the second day of testing, the colony was considered positive and was cloned. Cloning was carried out by limiting dilution in conditioned media into two 96-well plates, one with 5 cell/well and one plate with 1 cell/well. One week after cloning, single colony wells were tested by RIA. If all wells tested positive, the line was considered pure and was recloned a second time for stability. If all the wells did not test 100% positive, a positive well was used for the second cloning. The plates were tested again 7 days after the cloning. This procedure was repeated until all the clones tested 100% positive. The cells were then expanded in growth media and injected in injection media into the peritoneal cavity of Pristane-primed Balb/c mice at a concentration of about $3 \times 10^6$ hybridoma cells per mouse.

Prior to injection, supernatant from the cultured cells was used for isotyping by the Ouchterlony gel diffusion method, *Acta Path Microbiol Scand* 26:507 (1949). Ascites fluid was harvested from the mice about 10 days after the mice had been injected with the hybridoma cells. The ascites fluid was then titered by RIA and the IgG isotype content was measured using a Beckman ICS rate nephelometer.

The immunization protocol for generation of a Gent 3B1 monoclonal antibody was as follows. A female Balb/c mouse was injected intraperitoneally with 20 μg of the gentamicin BSA antigen in Freund's complete. One month later, 20 μg of gentamicin BSA was injected intravenously. Two weeks after that, 20 μg of gentamicin BSA was given in a combination of intravenous and intraperitoneal injection. Three days thereafter, the immunized mouse's spleen was removed and fusion was performed. The hybridomas so prepared were capable of producing monoclonal antibody with a specific affinity for gentamicin.

The immunization protocol for generation of GV AS5 monoclonal antibody was as follows. A female Balb/c mouse was injected intravenously with 1 μg of the gentamicin BSA antigen in Freund's complete. On day three, the mouse was injected with 139 μg of gentamicin BSA intravenously. On day four, the mouse was injected with 130 μg of gentamicin BSA intravenously. On day five, 139 μg of the gentamicin was injected intravenously. On day six, 139 μg of the gentamicin was again injected intravenously. On day seven, the immunized mouse's spleen was removed and fusion was carried out. The hybridomas so prepared were capable of producing monoclonal antibody with a specific affinity for gentamicin.

Two different monoclonal antibodies against gentamicin were prepared because gentamicin exists in several similar but not identical chemical species or isomers. Thus, an assay against gentamicin that uses monoclonal antibodies against two species of gentamicin permits a more accurate quantification of the amount of total gentamicin present.

17

Example 9

(Immunoreactivity of the Gentamicin-Biotin-Avidin Conjugate with a Gentamicin Antiserum)

The immunoreactivity of the gentamicin-biotin-avidin conjugates, obtained by following the procedure of Example 7, with a gentamicin antiserum was measured as follows. The gentamicin-biotin-avidin conjugate solutions were diluted in ICS™ diluent (Beckman) with 0.1% BSA to obtain five dilutions with 0.5, 0.4, 0.3, 0.2, and 0.1 mg/mL of avidin respectively. The ascites fluid containing anti-gentamicin monoclonal antibody obtained by following the procedure of Example 8 was filtered and diluted. Next, the gentamicin antiserum was diluted in the ICS diluent to obtain five antiserum dilutions of 1/5, 1/10, 1/15, 1/17.5, and 1/20 respectively.

The immunoreactivity assay was carried out on a ICS™ manual nephelometer (Beckman). The results obtained are shown in Table 1 below, indicating the clear and significant immunoreactivity of the gentamicin-biotin-avidin conjugates prepared with the gentamicin monoclonal antibody in the antiserum. OR indicates an over or out of instrument range reading.

TABLE 1

Absorption Rate Units Upon Cross-Titering a Prepared Gentamicin-Biotin-Avidin Conjugate with a Gentamicin Monoclonal Antibody Containing Antiserum

| Conj. Conc. | Antiserum Conc. | | | |
|---|---|---|---|---|
| (mg/mL) | 1/10 | 1/15 | 1/17.5 | 1/20 |
| 0.5 | OR | 3230 | 2530 | 2070 |
| 0.4 | OR | 3330 | 2530 | 2040 |
| 0.3 | OR | 3190 | 2645 | 2090 |
| 0.2 | 3140 | 2940 | 2790 | 2350 |
| 0.1 | 1230 | 1070 | 925 | 1010 |

Example 10

(Use of the Gentamicin-Biotin-Avidin Conjugate in a Competitive Inhibition Immunoassay with Known Amounts of Gentamicin)

Photometric immunoassays for gentamicin were carried out using the conjugates prepared by following the procedure of Example 7, using known amounts of gentamicin. Six calibrators with known amounts of gentamicin (0, 1, 2, 4, 8, and 12 µg of gentamicin per mL) were prepared. A Synchron CX® 5 clinical analyzer (Beckman) was used to measure the change in liquid medium turbidity as the competitive inhibition immunoassay reaction took place.

The rate of change of the cuvette liquid medium turbidity over time upon addition of the prepared immunoreactive conjugate was measured for each calibrator. The rate signals were plotted on a vertical axis against the gentamicin concentrations of the calibrators on the horizontal axis. Automatic comparison by the Synchron CX® 5 clinical analyzer of such calibration values obtained, with the initial rate of change of cuvette liquid medium turbidity caused by an unknown amount of gentamicin in a sample, permitted detection and quantification of the amount of gentamicin present per unit volume of the test sample.

The photometric rate signals detected were plotted on a vertical axis against the gentamicin concentrations of the six calibrators on the horizontal axis to establish a plot of light attenuation versus gentamicin concentration. The results obtained showed that the gentamicin-biotin-avidin conjugate prepared is useful for the detection and quantification of gentamicin in a competitive inhibition immunoassay.

Example 11

(Use of the Gentamicin-Biotin-Avidin Conjugate in a Competitive Inhibition Immunoassay with Unknown Amounts of Gentamicin)

The preconjugates prepared by the procedure set forth in Example 7 were used in separate competitive inhibition immunoassays carried out on a Synchron CX® 4 clinical analyzer (Beckman) to determine the amount of unknown gentamicin in serum samples from 51 different patients. In the immunoassay, 0.30 mg/ml of the conjugate was used.

The assay was repeated on the same 51 patient samples and compared with the results obtained on the same patient samples using: (1) a Synchron® turbidimetric clinical analyzer (Beckman) with a gentamicin immunoassay kit having a different gentamicin conjugate present; (2) an Array™ automated nephelometric analyzer, and; (3) an Abbott TDX™ florescent polarimization immunoassay (FPIA) instrument. The monoclonal antibody used for the immunoassays was the GVAS5 monoclonal antibody, diluted 1:4.

Example 12

(Preparation of Immunoreactive Tobramycin-Biotin-Avidin Conjugates)

A. Immunoreactive tobramycin-biotin-avidin conjugate were prepared as follows. Biotin tris aminohexanoic acid (10 mg, 0.017 mM, MW 582) was dissolved in a flask with 2 ml of dry DMF by being warmed in an oil bath at 75° C., following by being kept at this temperature for a further 10 minutes. CDI (3.5 mg, 0.0216 mM, MW 162) was then added to the flask, and the 75° C. temperature was maintained for a further 30 minutes, followed by stirring at room temperature for 2 hours. NHS (2.5 mg, 0.0217 mM, MW 115) was then added to the flask, and the room temperature stirring continued overnight.

Tobramycin (24 mg, 0.051 mM, MW 467.5) was then dissolved in 5 mL of dry DMF, and the activated biotin was added dropwise to the dissolved tobramicin with stirring at room temperature. The room temperature stirring was continued overnight. The solvent was then evaporated to dryness. The remaining solid residue was dissolved in a minimum amount of methanol, placed on a 1 cm by 30 cm chromatography column packed with a silica gel methanol slurry, and eluted with methanol and methanol/10% ammonium hydroxide. The appropriate fractions were collected, as determined, by TLC, to obtain 10 mg of a tobramycin-biotin preconjugate.

In this experiment the molar ratios of tobramycin to biotin to CDI/NHS used were 3:1:1.3.

The conjugate was then made by dissolving 50 mg of avidin in 2.5 mL of pH 7.4 phosphate buffer, 0.1M. HABA was used as previously set forth, to determine formation of the tobramicin-biotin-avidin conjugate. The conjugate was dialyzed against CBS with six changes of the buffer.

B. A second tobramycin-biotin-avidin conjugate was prepared as set forth above in this Example, but using molar ratios of tobramicin to biotin to CDI/NHS of 30:1:1.3.

An anti-tobramycin goat polyclonal antibody was used to determine the immunoreactivity and usefulness of the two conjugates prepared in competitive inhibition immunoassays for unknown amounts of tobramycin in test samples. Standard and calibration curves were established. It was determined that the two prepared tobramycin conjugates were both immunoreactive and suitable for use in immunoassays for tobramycin.

C. A third tobramycin-biotin-avidin conjugate was prepared as follows. The biotin tris aminohexanoic acid binding moiety (415 mg, 0.71 mM) was dissolved in a round bottom flask with a drying tube and 45 ml of dry DMF by being warmed in an oil bath at 70° to 75° C., following by being kept at this temperature for a further 15 minutes. CDI (140 mg, 0.86mM) was then added to the flask, and the 75° C. temperature was maintained for a further 30 minutes with stirring. After being cooled to room temperature, NHS (97 mg, 0.84 mM) was then added to the flask, an d the room temperature stirring of the solution continued for 20 hours.

Tobramycin (1000 mg, 2.14 mM) was then dissolved in 50 mL of 0.5M sodium bicarbonate, and the activated biotin was added through an addition funnel to the dissolved tobramicin over a period of 30 minutes with stirring at room temperature. The room temperature stirring was then continued for 24 hours. The solvent was then evaporated to dryness under reduced pressure. The remaining white solid residue was (3.45 g) was extracted twice with 100 mL of hot methanol (100 ml for each extraction), filtered, and evaporated to obtain 3.19 g of a white solid.

The 3.19 g of white solid was dissolved in 50 ml of methanol and absorbed into 5 g of silica gel. After removal of the solvent under reduced pressure, the silica gel was transferred to the top of a silica gel column (2.5 cm by 60 cm) containing 70 g of silica gel packed as a methanol slurry. The column was then eluted with 700 ml of m ethanol to remove excess biotin tris aminohexanoic acid, followed by elution with 600 ml of methanol with 10% ammonium hydroxide. Column fractions were monitored by TLC using methanol with 10% ammonium hydroxide, and fractions judged appropriate by positive reaction to cinnamaldehyde spray, were pooled to yield 370 mg of a third preconjugate. Conjugation to avidin was carried out as previously set forth, followed by a determination by the methods already given, that the third conjugate was also immunoreactive and suitable for use in a competitive inhibition immunoassay for tobramycin.

The molar ratios of tobramycin to biotin to CDI/NHS used to prepare the third preconjugate were 3:1:1.2.

For all the tobramycin-biotin preconjugates prepared as set forth above, it was clear that the reaction between the activated biotin ester and the tobramicin resulted in an excess of the amount of the tobramicin preconjugate that could be used to make an immunoreactive tobramicin conjugate (i.e. biotin binding moiety joined to an immunoreactive species of the tobramicin), as compared to the amount of tobramicin preconjugate that could not be used to make an immunoreactive tobramycin conjugate (i.e. biotin binding moiety joined to a nonimmunoreactive species of the tobramycin)

Thus, for example, a visual inspection of the relative size of the TLC spots of reaction product, showed that the spot of immunoreactive tobramycin species preconjugate was larger than the TLC spot of the nonimmunoreactive tobramycin species preconjugate. Examination of the relative size of the TLC spots (followed by conjugation with avidin of at least the major product (large TLC spot) and subsequent immunoreactivity study on at least the major product) showed that the yield of the desired preconjugate was in excess as compared to the yield of the undesired preconjugate. Specifically, for the reaction parameters specified the relative area of the immunoreactive tobramycin species preconjugate TLC spot:nonimmunoreactive tobramycin species preconjugate TLC spot varied from about 2:1 to about 5:1.

Tobramycin:biotin ratios of 5:1, 10:1, 15:1. 20:1, 25:1, and various intermediate concentration ratios can be used in the method set forth above. It can be reasonably expected that the reaction products obtained by such alternate analyte:binding moiety ratios would yield preconjugates that could be used to make immunoreactive conjugates.

Additionally, the tobramycin (polymorphic analyte):CDI (coupling reagent) ratios can, it is reasonably postulated, be varied to any ratio between about 0.5:1 and about 30:1 with results comparable to those set forth above.

Example 13

(Preparation of a Biotinylated Amikacin Preconjugate)

A biotinylated amikacin preconjugate was prepared as follows. Biotin tris aminohexanoic acid activated with CDI/NHS in DMF, was reacted overnight with amikacin dissolved in 0.5M sodium bicarbonate, followed by elution of the preconjugate by column chromatography.

Preconjugates so prepared were conjugated to avidin and were found to exhibit similar immunoreactivities towards anti-amikacin antibodies and were determined to be useful as inhibitors in competitive inhibition immunoassays for amikacin in serum test samples.

Several amikacin-biotin preconjugates suitable for preparing immunoreactive conjugates were made by activating a biotin binding moiety with CDI/NHS in DMF followed by addition of amikacin in 0.5M NaHCO$_3$. The coupling of amikacin and biotin was carried out overnight. The molar ratios of the reactants used was amikacin:biotin:CDI/NHS 5:1:1.2. Column chromatography as carried out using a 10% NH$_4$OH/MeOH elution.

Amikacin was reacted with a biotin tris aminohexanoic acid binding moiety to prepare an amikacin preconjugate as follows.

Biotin tris aminohexanoic acid binding moiety (MW 582, 1 g, 1.72 mM) was dissolved in 100 ml dry DMF by warming at 75° C. CDI (334 mg, 2.08 mM) was then added and stirred at this temperature for 30 minutes, followed by stirring at room temperature for 2 hours. Then NHS (235 mg, 2.04 mM) was then added and stirring was continued overnight at room temperature.

Amikacin (MW 585, 5 g, 8.55 mM) was dissolved in 80 mL of 0.5M NaHCO$_3$ and the activated biotin ester was then added slowly through a funnel. After 15 minutes 40 mL of 0.5M NaHCO$_3$ was added along with 10 mL of water. Stirring was then continued overnight at room temperature.

The solvent was then evaporated completely to obtain 12.15 g of a solid. This solid was extracted with 200 ml MeOH (100 ml each) heated and filtered. The filtrate was evaporated until dried to obtain 6.29 g of a solid. The solid was dissolved in methanol and adsorbed onto 8.5 g of silica gel and was loaded on a silica gel column packed in MeOH. Eluted fractions were followed by TLC. Appropriate fractions were pooled and evaporated to obtain 570 mg of the desired amikacin-biotin preconjugate. The ratio of amikacin:biotin:CDI:NHS used as 5:1:1.2:1.2

The experiment set forth immediately above was repeated using an amikacin:biotin:CDI:NHS ratio of 0:1:1:3:1.3, and replacing the sodium bicarbonate by DMF. The column eluent used as 10% ammonium hydroxide ($NH_4OH$) in methanol. It was found that not using a carbonate such as sodium bicarbonate made the amikacin preconjugate reaction product more difficult to isolate.

Amikacin:biotin ratios of 5:1, 10:1, 15:1. 20:1, 25:1, and various intermediate concentration ratios can be used in the method set forth above. It can be reasonably expected that the reaction products obtained by such alternate analyte-:binding moiety ratios would yield preconjugates that could be used to make immunoreactive conjugates.

Additionally, the amikacin (analyte):CDI (coupling reagent) ratios can, it is reasonably postulated, be varied to any ratio between about 0.5:1 and about 30:1 with results comparable to those set forth above.

Example 14

(Conjugation of an Amikacin-Biotin Preconjugate to Avidin)

100 mg avidin (Boehringer Manheim GmbH) was dissolved in 5 mL of phosphate buffer, 0.1M, pH 7.4. HABA was used as a color indicator. 580 mg of the amikacin preconjugate dissolved in 25 ml of 1:1 MeOH/$H_2O$, was added in 100 µL aliquots, for a total of 600 µL. The color of the solution changed from pink-orange to light yellow. 5 ml of phosphate buffer was then added and the solution was dialyzed against CBS with three changes.

The disclosed method for making immunoreactive conjugates has many advantages, including the following:

1. A consistently high yield of polymorphic analyte preconjugates useful for preparing immunoreactive conjugates can be obtained.
2. A stoichiometric excess of preconjugate comprising the immunogenic species of the polymorphic analyte relative to the amount of preconjugate comprising the nonimmunogenic species of the polymorphic analyte, can be obtained by the present method, except for the aminoglycoside antibiotic amikacin.
3. The aminoglycoside antibiotic amikacin can be easily isolated from other reaction products by using a carbonate in the reaction medium.
4. The disclosed methods can be carried out under mild conditions.

Although the present invention has been described in detail with regard to certain preferred embodiments, other embodiments, version, and modifications are within the scope of the disclosed invention. For example, the polymorphic analytes are not restricted to only certain aminoglycoside antibiotics. Furthermore, the preconjugate can be made using a variety of coupling reagents and binding moieties.

Accordingly, the spirit and scope of the following claims should not be limited to the descriptions of the specific embodiments of the present invention set forth above.

We claim:

1. A method for making an immunogenic aminoglycoside preconjugate mixture, useful for preparing immunoreactive aminoglycoside conjugates capable of participating in an immunoprecipitation reaction in an immunoassay for the aminoglycoside, wherein the aminoglycoside is polymorphic and is selected from a group consisting of gentamicin, tobramycin and amikacin, the method comprising the steps of:

(a) joining a spacer compound with biotin to form a binding moiety;

(b) activating the binding moiety in a dimethylformamide (DMF) solvent with coupling reagents carbonyldiimidazole (CDI) and N-hydroxysuccinimide (NHS);

(c) reacting the activated binding moiety with an aminoglycoside in a reaction medium selected from a group consisting of DMF and bicarbonate to form aminoglycoside preconjugates comprising immunogenic aminoglycoside preconjugates which are capable of resulting in an immunoreactive aminoglycoside conjugate, and nonimmunogenic aminoglycoside preconjugates which are not capable of resulting in an immunoreactive aminoglycoside conjugate, wherein the molar ratio of the aminoglycoside to the binding moiety present at the beginning of the reacting step is between about 0.5:1 and about 5:1, and wherein when the aminoglycoside is amikacin, the reaction medium is bicarbonate;

(d) separating by chromatography an immunogenic aminoglycoside preconjugate mixture that is capable of resulting in an immunoreactive aminoglycoside conjugate from a nonimmunogenic aminoglycoside preconjugate mixture that is not capable of resulting in an immunoreactive aminoglycoside conjugate; wherein the separating step comprises a step of eluting with a blend of methanol and ammonium hydroxide the immunogenic aminoglycoside preconjugate mixture.

2. The method of claim 1, wherein the aminoglycoside is gentamicin, and the reaction medium of step (c) is DMF.

3. The method of claim 1, wherein the aminoglycoside is tobramycin.

4. The method of claim 1, wherein the aminoglycoside is gentamicin or tobramycin, and wherein the method results in a stoichiometric excess of immunogenic aminoglycoside preconjugates relative to the amount of nonimmunogenic aminoglycoside preconjugates.

5. The method of claim 4, wherein the method results in a ratio of immunogenic aminoglycoside preconjugates to nonimmunogenic aminoglycoside preconjugates of about 2:1.

6. The method of claim 4, wherein the method results in a ratio of immunogenic aminoglycoside preconjugates to nonimmunogenic aminoglycoside preconjugates of about 3:1.

7. The method of claim 4, wherein the method results in a ratio of immunogenic aminoglycoside preconjugates to nonimmunogenic aminoglycoside preconjugates of about 4:1.

8. The method of claim 4, wherein the method results in a ratio of immunogenic aminoglycoside preconjugates to nonimmunogenic aminoglycoside preconjugates of about 5:1.

9. The method of claim 1, wherein the molar ratio of the aminoglycoside to the binding moiety present at the beginning of the reacting step (c) is between about 1:1 and about 3:1.

10. The method of claim 1, wherein the reacting step (c) is carried out at a temperature between about 15 C. and about 30 C.

11. The method of claim 1, wherein the reacting step (c) is carried out for between about 10 hours and about 60 hours.

12. A method for making an immunogenic amikacin preconjugate mixture, useful for preparing immunoreactive amikacin conjugates capable of participating in an immunoprecipitation reaction in an immunoassay for amikacin, the method comprising the steps of:

(a) joining a spacer compound with biotin to form a binding moiety;

(b) activating the binding moiety in a dimethylformamide (DMF) solvent with coupling reagents carbonyldiimidazole (CDI) and N-hydoxysuccinimide (NHS);

(c) reacting the activated binding moiety with amikacin in bicarbonate solvent to form amikacin preconjugates comprising immunogenic amikacin preconjugates which are capable of resulting in an immunoreactive amikacin conjugate, and nonimmmunogenic amikacin preconjugates which are not capable of resulting in an immunoreactive amikacin conjugate, wherein the molar ratio of the amikacin to the binding moiety present at the beginning of the reacting step is between about 0.5:1 and about 5:1; and (d) separating by chromatography an immunogenic amikacin preconjugate mixture that is capable of resulting in an immunoreactive amikacin conjugate from a non-immunogenic amikacin preconjugate mixture that is not capable of resulting in an immunoreactive amikacin conjugate; wherein the separating step comprises a step of;

eluting with a blend of methanol and ammonium hydroxide the immunogenic amikacin preconjugate mixture.

13. The method of claim 12, wherein the reacting step (c) is carried out at a temperature between about 15 C. and about 30 C.

14. The method of claim 12, wherein the reacting step (c) is carried out for between about 10 hours and about 60 hours.

* * * * *